United States Patent [19]
Chapman et al.

[11] Patent Number: 5,520,924
[45] Date of Patent: May 28, 1996

[54] METHODS AND ARTICLES FOR ADMINISTERING DRUG TO THE ORAL CAVITY

[75] Inventors: Robert J. Chapman, Boston; Charles M. Habib, Haverhill, both of Mass.

[73] Assignee: Mizu Systems Corporation, Midland, Mich.

[21] Appl. No.: 89,706

[22] Filed: Jul. 9, 1993

[51] Int. Cl.$^6$ .............. A61K 9/14; A61K 47/34; A61C 15/04
[52] U.S. Cl. .............. 424/435; 424/487; 514/772.2; 514/953; 514/965; 132/323; 132/329
[58] Field of Search .............. 424/435, 486, 424/487, 78.37; 514/772.2, 953, 965; 132/323, 329

[56] References Cited

U.S. PATENT DOCUMENTS

| | | | |
|---|---|---|---|
| 3,076,218 | 2/1963 | Cook et al. | 15/207.2 |
| 4,663,358 | 5/1987 | Hyon et al. | 521/64 |
| 4,851,168 | 7/1989 | Graiver et al. | 264/28 |
| 5,098,711 | 3/1992 | Hill et al. | 132/323 |

FOREIGN PATENT DOCUMENTS

| | | |
|---|---|---|
| 903540 | 2/1986 | Belgium . |
| 58-099411 | 6/1983 | Japan . |
| 59-110613 | 6/1984 | Japan . |
| 63-220804 | 9/1988 | Japan . |
| 5096597 | 4/1993 | Japan . |

OTHER PUBLICATIONS

"Volatile Oils", pp. 422–425, Remington's Pharmaceutical Sciences, 17th Edition, 1985.
"Controlled Release of Fluoride from Hydrogels for Dental Applications", D. R. Cowsar et al., Southern Research Institute, pp. 180–197.
"Airvol Polyvinyl Alcohol", Air Products.
"High Strength Hydrogels (A New Material)", Dow Corning.
Patent Abstracts of Japan, Oct. 16 1984, vol. 8, No. 225 (C–247) Database WPI, Week 8843, Derwent Publications Ltd., London, GB; AN 88–302559.
Database WPI, Week 9320, Derwent Publications Ltd., London, GB; AN 93–163934.
Patent Abstracts of Japan, Sep. 06 1983, vol. 7, No. 201 (C–184).

*Primary Examiner*—Carlos A. Azpuru
*Attorney, Agent, or Firm*—Wolf, Greenfield & Sacks

[57] ABSTRACT

The present invention features methods and articles of manufacture for delivering drug to the oral cavity. The methods and articles feature drug held in a polyvinyl alcohol matrix. The matrix releases the drug in a sustained constant manner.

10 Claims, 6 Drawing Sheets

METHODS AND ARTICLES FOR ADMINISTERING DRUG TO THE ORAL CAVITY

FIELD OF THE INVENTION

The present invention relates generally to methods and articles of manufacture for delivering drug to the oral cavity. Embodiments of the present invention feature polyvinyl alcohol hydrogels capable of drug release over an extended period of time.

BACKGROUND OF THE INVENTION

Attempts to treat acute and chronic disease states of the oral cavity with topical medications, and attempts to administer drugs for nonlocal disease states using the oral cavity to absorb drug have been hampered by the difficulty in maintaining a constant sustained release of an effective amount of drug.

With respect to the treatment of local diseases of the oral cavity, fluoride has been found effective in reducing the incidence of carious lesions in teeth. However, not all drinking water is fluoridated. In those areas where drinking water is not fluoridated, an alternate means for applying fluoride in a routine sustained manner is necessary.

With respect to the treatment of nonlocal disease states, cardiovascular drugs are often administered through the oral cavity as sublingual or buccal tablets. However, the time duration of the release of drugs is typically short. Current trends in therapy suggest greater control over angina is accomplished with long term administration of drug at lower doses.

Nicotine and nicotine substitutes are administered for absorption in the oral cavity as a deterrent to smoking. One method of administering nicotine is to incorporate nicotine in a gum base. The gum base releases nicotine in response to chewing. These gums tend to release drugs in a nonlinear manner. The patient must be cautioned to refrain from chewing a fresh stick of gum extensively due to the sudden release of nicotine. The sudden release of nicotine can cause headache and dizziness.

Polyvinyl alcohol compositions have been suggested for application for fabrication into films, tubing, fibers, contact lenses, and other medical prostheses, as control release vehicles for drugs, and other biological materials. See: U.S. Pat. No. 4,851,168.

However, there remains a need for a method and article of manufacture to deliver and release a sustained constant dose of drug to the oral cavity for local and nonlocal disease states and treatments.

SUMMARY OF THE INVENTION

The present invention features methods and articles of manufacture for delivering and releasing a sustained dose of drug to the oral cavity. One embodiment of the present invention features an article of manufacture comprising a drug held in a polyvinyl alcohol matrix formulated for application to the oral cavity. The polyvinyl alcohol matrix releases an effective amount of drug in a constant, sustained manner in the presence of oral secretions.

Polyvinyl alcohol is formed from vinyl acetate monomer. The monomer is polymerized to form polyvinyl acetate and, thereafter, converted to polyvinyl alcohol. The physical properties of polyvinyl alcohol are influenced by the degree of hydrolysis.

The term "formulated for application to the oral cavity" is used to suggest that the drug has no noxious tastes or if the drug has a noxious taste, the taste is masked with appropriate flavoring agents. The term is also used to suggest that the matrix has an appropriate size and shape to be received in the oral cavity. By way of example, the matrix may have the size and shape of a troche, lozenge and the like. An effective amount is an amount of a drug or substance which causes the desired therapeutic result.

A preferred article of manufacture comprises a polyvinyl alcohol matrix in the form of a fiber or a bead. The term fiber is used in a conventional sense to refer to an elongated filamentous structure. The term "bead" is used in a general sense to refer to small structures, comprising any geometric shape or form capable of being placed in the oral cavity.

The fiber can be incorporated into a toothbrush as a bristle. One embodiment of the present article features a drug comprising fluoride. The brush is used to apply fluoride to the teeth in an effective amount as the teeth are brushed in a conventional manner.

One embodiment of the present invention features a fiber of a polyvinyl alcohol matrix combined with one o more fibers having a composition other than polyvinyl alcohol. The fibers having a composition other than polyvinyl alcohol impart mechanical properties of stiffness to the brush.

One embodiment of the present article features a fiber having drug held in a polyvinyl alcohol matrix woven with other fibers. The other fibers have a similar composition or have compositions to impart special properties and features. One embodiment of the present invention features a woven pad having fibers having drug held in a polyvinyl alcohol matrix. The woven pad can be applied to lesions and wounds of the oral cavity. One embodiment features a drug comprising an antimicrobial agent, to allow the pad to treat infections of wounds or lesions.

The fiber can be woven or spun with similar fibers or with other fibers with different mechanical properties, for use as line, floss, sutures, or the like. One embodiment of the present article features a drug comprising fluoride, The floss or line can be used to apply fluoride to the teeth as the teeth are flossed in a conventional manner.

One embodiment of the present article features drug held in a polyvinyl alcohol matrix in the form of a bead. The bead can be made in the form of a troche, lozenge and the like. The bead releases drug in effective concentrations over a prolonged period of time. Such articles are ideally suited to deliver drugs which are readily absorbed from buccal and sublingual areas of the oral cavity such as nitroglycerin, isoproterenol hydrochloride and erythrityl tetranitrate. Such articles are also ideally suited for the delivery of nicotine and nicotine substitutes as smoking deterrants.

Surprisingly and unexpectedly, the polyvinyl alcohol matrix has a release pattern that is independent of the chewing or physical grinding of the bead. Thus, drug can be delivered to the oral cavity without concern that a patient will influence the release by physical activity.

Articles of the present invention are ideally suited for the application of antimicrobial agents into the oral cavity. Typical antibacterial agents which are incorporated into the polyvinyl alcohol matrix comprise chloroamine-T, boric acid, gentian violet, methylene blue, formaldehyde, sodium hypochloride, iodine compounds, chromic acid, silver nitrate, zinc chloride, aluminum acetate, phenol, cresol, eugenol, and cetyl pyridinium chloride.

Articles of the present invention are also ideally suited for treating pain and irritation of the oral cavity. Typical anesthetics which are incorporated into the polyvinyl alcohol matrix include tetracaine, dibucaine, benzocaine, butacaine, dyclonine, and tripelennamine.

Articles of the present invention are also suitable for the control of dental caries and plaque. Embodiments of the present invention can apply a fluoride treatment during typical teeth brushing or flossing procedures. Preferred drugs held in the polyvinyl alcohol matrix comprise sodium fluoride, stannous fluoride quarternary ammonium compounds, essential oils, sanguinarine and bisbiguanides. Typical bisbiguanides include chlorhexadine and alexidrine.

A further embodiment of the present invention features a method of delivering and releasing an effective dose of drug to the oral cavity. The delivery of drug to the oral cavity can be for a local treatment of a disease of the oral cavity, or a nonlocal or systemic treatment of a disease. One method comprises the step of administering to the oral cavity of a subject, a drug held in a polyvinyl alcohol matrix. The polyvinyl alcohol matrix releases the drug in a consistent, sustained manner in the presence of oral secretions.

The term "subject" is used in the sense of an animal or human having a disease state or potential disease state which is to be treated.

One embodiment of the present invention features administering the drug in a polyvinyl alcohol matrix in the form of a fiber or a bead. For example, one method of administering a drug held within a polyvinyl alcohol matrix is to incorporate such a fiber in a toothbrush as a bristle or to incorporate such fiber into a floss. The drug is administered as the subjects' teeth are brushed or flossed.

The fiber can be woven with other fibers to form a pad or a fabric. The pad or the fabric can be placed in the oral cavity where the drug is released in the presence of oral secretions.

One example of administering drug held within a polyvinyl alcohol matrix is to formulate such bead as a troche, lozenge or incorporate such beads in a gum base. The drug is released while the bead is present in the oral cavity of the subject. Surprisingly and unexpectedly, the present invention provides a sustained constant release of drug independent of the mastication of the bead by the subject.

Embodiments of the present invention are ideally suited for the delivery of drugs such as antimicrobial agents; antiplaque and anticaries agents such as fluorine salts and bisbiguanides; nicotine and nicotine substitutes; and cardiovascular drugs such as nitroglycerin and isoproterenol.

Other features and advantages of the present invention will be apparent from the following description which, by way of illustration, shows preferred embodiments of the present invention and the principles thereof and what is now considered to be the best mode to apply these principles.

DETAILED DESCRIPTION

The present invention is described in detail as a method and apparatus for administering drug to the oral cavity, with the understanding that the present disclosure is to be considered an exemplification of the principles of the invention and is not intended to limit the invention to the embodiment illustrated. The present invention can be used wherever it is desired to deliver and release an effective amount of drug to the oral cavity. By way of example, without limitation, the present invention has applications for the delivery of antimicrobial agents, nicotine and nicotine substitutes, and cardiovascular drugs.

Figure 1:
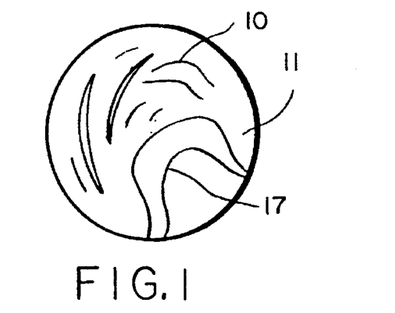
FIG. 1 is a view of a bead in partial cutaway embodying features of the present invention.

Turning now to FIG. 1, an article of manufacture for delivering a drug to the oral cavity, is designated by the numeral 11. Article 11 is comprised of a drug held in a polyvinyl alcohol matrix. As illustrated, article 11 is spherical having a outer surface 15 and an interior area 17 shown in cutaway. Article 11 may have any shape desired. To appeal to children, article 11 may be shaped in forms such as animals, characters and inanimate objects.

A drug is dispersed throughout the polyvinyl alcohol matrix of article 11 or can be dispersed with greater concentration towards the interior area 17 or the outer surface 15 to influence release rates. Article 11 is formulated for application to the oral cavity. The article is sized to be received in the oral cavity in the manner of a troche. The drug comprises, by way of example, antimicrobial substances, antiplaque and anticaries substances, nicotine and nicotine substitutes, and cardiovascular substances.

One preferred drug comprises fluoride to prevent cavities and plaque. The polyvinyl alcohol matrix releases fluoride in a constant sustained manner in the presence of oral secretions.

Article 11 releases drug in a predetermined manner. The rate of release of the drug from the polyvinyl alcohol matrix may be influenced by the manner in which the drug is incorporated in the polyvinyl alcohol matrix. The drug may have a distribution in which drug molecules are distributed towards the exterior 15 or the interior 17. The drug may be incorporated in large or small crystals.

Surprisingly and unexpectedly, physical abrasion kneading has little effect on the release profile of the article 11. Thus, in the presence of chewing and mouth movements, drug is released in a substantially constant rate.

Figure 2:
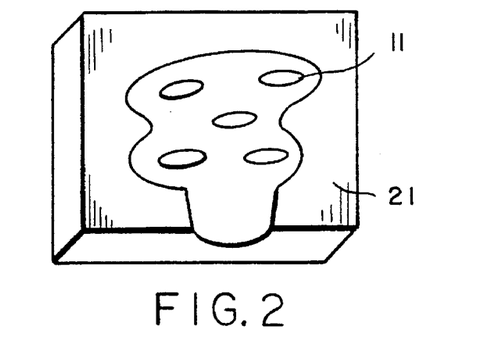
FIG. 2 is a top view depicted in partial cutaway beads of polyvinyl alcohol matrix with drug incorporated therein placed in a rectangularly shaped gum base.

Article 11 or a plurality of articles 11 of suitable small size can be placed in gum base 21 as illustrated in FIG. 2. Each article 11 provides a sustained release of drug into the oral cavity in the presence of oral secretions. Gum base 21 holds each article 11 in a cohesive mass as the gum base 21 is chewed by the subject.

The base 21 is ideally suited for the delivery of nicotine and nicotine substitutes into the oral cavity. The gum base allows the subject to obtain some oral gratification from the chewing process as the nicotine or nicotine substitute is released from the beads.

In operation, the article 11, formulated as a lozenge, troche, or incorporated in a gum base is placed in a subject's oral cavity. Drug is released in a sustained effective dose.

Figure 3:
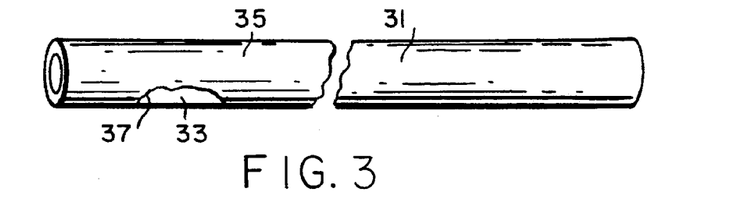
FIG. 3 is a fiber having a drug held in a polyvinyl alcohol matrix.
Figure 4:
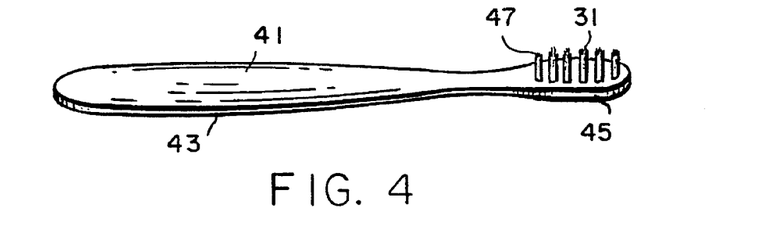
FIG. 4 is a side view of a toothbrush having a fiber having a drug incorporated within a polyvinyl alcohol matrix.

A further embodiment of the present invention features a fiber 31, as best illustrated in FIG. 3. The fiber is comprised of a drug held in a polyvinyl alcohol matrix 33. The matrix has an exterior area 35 and an interior area 37. The interior area 37 can be formed as a core and the exterior area as a shell. The drug may comprise sodium fluoride or other agents for application to the mouth. Fiber 31 can be incorporated into a toothbrush 41, as best illustrated in FIG. 4. Brush 41 is comprised of a handle portion 43 and a head portion 45. Head portion 45 contains at least one fiber 31 comprising drug held in a polyvinyl alcohol matrix.

The fiber 31 can be incorporated with a plurality of similar fibers or in combination with fibers having a different composition 33, to impart special features and physical characteristics to the brush. For example, the fiber 31 can be combined with nylon bristles to impart stiffness to the brush.

In operation, a subject brushes their teeth with the brush 41 in a conventional manner. Fluoride is released from bristle 31 during the brushing process.

Figure 5:
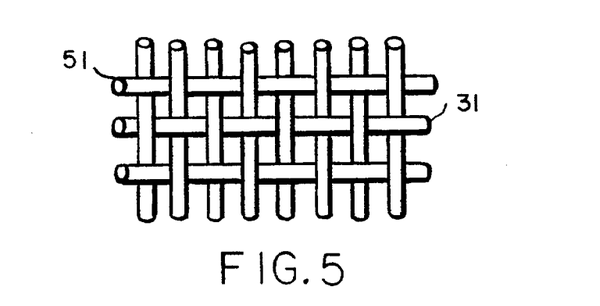
FIG. 5 is a top view of a portion of a woven pad having a drug held in a polyvinyl alcohol matrix, shaped in the form of a fiber.

Fiber 31 may also be incorporated into a woven article generally designated by the numeral 51, as illustrated in FIG. 5. The woven article 51 has a fiber 31 having drug held in a polyvinyl matrix. Woven article 51 is ideally suited to form pads. Such pads can be used for packing or stuffing wounds of the oral cavity. Preferred drugs held in the matrix comprise, by way of example, antimicrobial substances such as chlorohexadrine and alexidrine.

In operation, the woven article 51 is applied to the wound in a conventional manner. An effective amount of the drug is released in a sustained manner from fiber 31.

Figure 6:
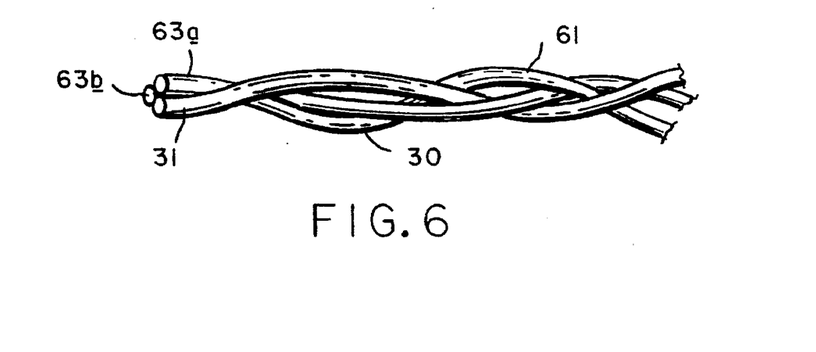
FIG. 6 is a line comprised of a plurality of fibers in which one of the fibers has a drug incorporated within a polyvinyl alcohol matrix.

The fiber 31 can be spun with other fibers to form a line or string 61, as best illustrated in FIG. 6. Fiber 31 is spun with fibers 63a and 63b to form string 61. String 61 is suitable for dental floss. Fiber 31 comprises a drug held in a polyvinyl alcohol matrix 33. A preferred drug is a fluoride salt, or antimicrobial agents.

String 61 can also be used as suturing material to close wounds and openings.

In operation, as a floss, string 61 is used in a conventional manner. During such use, an effective amount of drug, such as fluoride, is released from the polyvinyl alcohol matrix.

The present examples exemplify features of the present invention.

EXAMPLE 1

This example features the formation of fibers having a drug held in a polyvinyl alcohol matrix. Four fibers having sodium fluoride held in a polyvinyl alcohol matrix were made. Techniques for forming fibers of polyvinyl alcohol are discussed in U.S. Pat. No. 4,851,168.

In general, a solution of PVA in a 1:4 weight ratio mixture of water and dimethylsulfoxide (DMSO) is prepared and extruded through the an orifice into a coagulation bath composed of an alcohol and maintained at −40° C. Residual DMSO is then extracted from the collected gel fibers followed by removing the alcohol and then drawing the dried fibers at elevated temperature (160° C.) to the desired draw ratio.

Fiber 1

A fiber, designated as fiber #1, was made with a core/shell structure. NaF was dispersed in the PVA dope solution (10:1 PVA to NaF on a weight basis). This PVA/NaF dope was then co-extruded as the core together with a PVA solution that did not include NaF for the shell. A fine dispersion of NaF was obtained since the solubility of this salt is very small when DMSO is used. DMSO was used in order to obtain the desired T-PVA morphology. Since the core PVA solution that contained NaF was viscous in nature, no precipitation was observed throughout the spinning process and the rate of NaF into the fibers appears constant and uniform.

After extraction of the solvents, a clear core/shell structure was observed by SEM and the corresponding mapping of the sodium element. Energy dispersive spectroscopy (EDS) data from the surface of the fiber and around the center of its cross-sectional area confirmed that there was no sodium (or fluoride) on the surface compared to a large concentration in the interior.

The fiber was then drawn between two reels rotating at different speeds to give a draw ratio of 12.5 and a final diameter of 220 μm. The surface of this fiber appeared smooth (other than the markings parallel to the fiber axis which occurred by contact with the spinnerete wall during the spinning process). Very few aggregates of NaF were observed along the surface of the fiber. EDS spectra taken again on the surface and near the center indicated a very small sodium concentration on the surface compared to a much higher concentration in the interior of the fiber.

Fiber 2

A fiber, designated fiber #2, was made with a homogeneous distribution of NaF in the PVA matrix. NaF was incorporated into the PVA dope before spinning. The composition that was used to spin fiber is identical to that used as the core of fiber #1. The spinning parameters were similar to those used for fiber #1.

After extraction of the solvents, SEM and elemental mapping indicated a homogeneous distribution of NaF in the PVA matrix. Further, the NaF salt appeared as a fine grain size dispersion with no significant large aggregates. EDS spectra confirmed that the concentration of sodium near the edge and around the center was very similar.

This fiber was then drawn as before between two reels rotating at different speeds. However, because this fiber was weaker than fiber #1 (most likely because of the presence of larger concentration of NaF), a draw down ratio of only 8 was used resulting in a final diameter of 700 μm. The surface of this fiber was relatively rough with a higher concentration of NaF.

Fiber 3

A third fiber, designated fiber #3, having a core/shell fiber, was prepared in a similar way to fiber #1. However, in order to increase the concentration of NaF in the fiber, a saturated aqueous solution of this salt was used which was then combined with DMSO and PVA as the dope for the core of the fiber. Further, as is detailed later, the crystallinity of this fiber was set lower than fiber #1 in order to increase the rate of diffusion.

The core/shell morphology suggested that the NaF was included only in the core of the fiber with no local aggregation of the salt in the PVA matrix.

The fiber was then drawn between two reels as described before to a draw ratio of 12 to give a final fiber diameter of 290 μm. Very little NaF was observed on the surface of the fiber and the general features of the surface were similar to those observed with fiber. Indeed, EDS spectra and SEM confirmed the core/shell structure where the NaF grains were found only in the interior of the fiber.

Fiber 4

A fourth fiber, designated fiber #4, was made with NaF loaded into the polyvinyl alcohol matrix by swelling the matrix in a saturated NaF solution, then precipitating the NaF salt inside the fiber. A significant amount of NaF was incorporated into the fiber. However, large NaF aggregates were obtained giving rise to a very heterogeneous distribution of the salt in the PVA matrix. The results of EDS analysis were dependent on the location the beam was focused on the fiber. The analysis suggested a large Na concentration when the beam was focused around an aggregate and no Na between aggregates.

Draw down of the fiber was difficult and only a draw ratio of about 8 could be achieved with this concentration and distribution of NaF in the PVA fiber to yield a fiber diameter of 500 µm. The surface of the drawn fiber presented large salt aggregates at the surface. SEM taken from a cross-section of this fiber indicated a larger concentration of NaF immediately adjacent to the outer surface of the fiber.

A summary of these fiber morphologies, NaF concentration, and the final diameter of the fiber (which is proportional to the degree of orientation, mechanical properties, water pick-up, etc.) is listed in Table 1.

TABLE 1

Summary of selected properties from the NaF filled PVA fibers.

| Fiber | Fiber diameter | Initial NaF concentration [mg/gr PVA] | Structure | Rate | % Swell in water |
|---|---|---|---|---|---|
| #1 | 220 | 17.96 | core/shell | 0.139 | 17.4 |
| #2 | 700 | 29.47 | homogeneous NaF during spinning | 0.235 | |
| #3 | 290 | 26.41 | core/shell structure | 0.577 | 44.7 |
| #4 | 500 | 48.81 | homogeneous NaF swelling after spinning | 0.567 | |

EXAMPLE 2

Experiments were conducted to determine the profile of release and the release rate. The release experiment was conducted by placing a known weight (about 0.25 gr) of fiber in 200 ml deionized water at room temperature under continuous stirring and measuring the conductance of the water using a model 31 conductivity bridge manufactured by Yellow Spring Instrument Company. Conductivity readings were taken until no change was observed for about 15 minutes.

Figure 7:
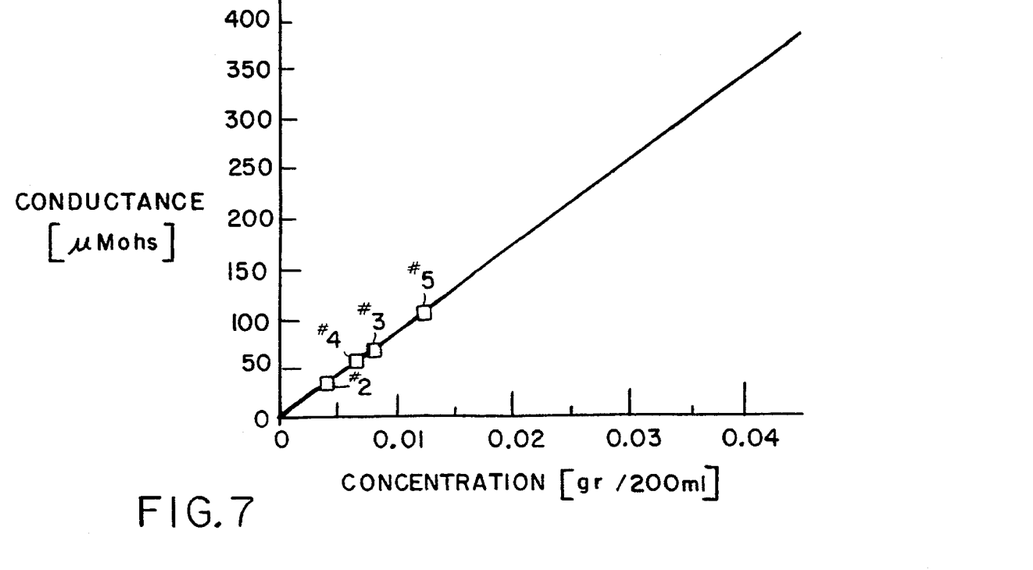
FIG. 7 is a calibration curve of conductance versus concentration of NaF.

A calibration curve, correlating the conductance of NaF with its concentration under identical experimental conditions, was constructed. This calibration curve is depicted in FIG. 7. Points marked with small open squares and labelled with #2, #3, #4, and #5 reflect NaF in PVA. The point at #2 represents 1.80% NaF in PVA, #3 represents 2.95% NaF in PVA, #4 represents 2.67% NaF in PVA and #5 represents 4.88% NaF in PVA. The effect of soluble PVA on the conductance of NaF solution was negligible in the concentration range that was studied. Using this calibration curve the total concentration of NaF in the PVA fibers were determined.

Figure 8:
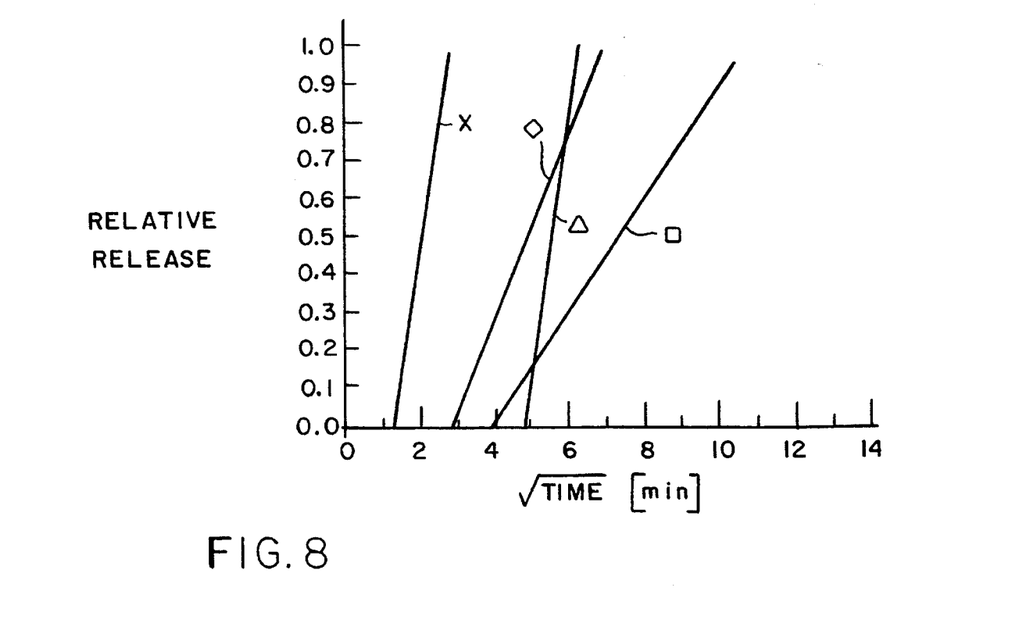
FIG. 8 depicts graphically relative release of NaF against the square root of time.

FIG. 8 is a summary of the results where the relative release of NaF is plotted against the square root of time. The relative release was derived in the usual way from the ratio $(C_t-C_o)/(C-C_o)'$ where $C_t$ is the conductance (or concentration) at time t, $C_o$ is the conductance of the distilled water, and C' is the final conductance of the solution after all NaF was released from the fiber. As used in the figure, squares represent fiber #1, diamond represents Fiber #2, triangles represent fiber #3, and Xs represent fiber #4.

The release profile of NaF from all the PVA fibers follows a typical Fick's law as can be observed from the large linear segment in FIG. 8. The release rates, which were computed from the slope of the linear segment, are set forth below in Table 2.

TABLE 2

Slope of Linear Release Segment.

| | Slope |
|---|---|
| Fiber #1 | 0.139 ± 0.005 |
| Fiber #2 | 0.235 ± 0.006 |
| Fiber #3 | 0.577 ± 0.004 |
| Fiber #4 | 0.567 ± 0.018 |

It is evident that the release rate does not depend only on the type of morphology but also on the degree of orientation. The degree of orientation, determined by the draw ratio, affects the degree of crystallinity which determines the degree of swelling of the PVA and hence the release rate of the NaF.

FIG. 8 also shows that the release profile consists of two regions; a slow release rate during an induction period followed by a much faster, linear release rate. The induction period depends primarily on the type of morphology of the fiber. That is, in the homogeneous fibers (#4 and #3) constant release rate is obtained faster (shorter induction time)than in the fibers with the core/shell morphology. Further, this time is faster for fiber #4 than fiber #2 as NaF appears to have aggregated in a large concentration near or on the surface of the fibers. Evidently, in the fibers with the core/shell structure, NaF must first dissolve and then diffuse the release rate of NaF that was absorbed into the fiber after it was formed, is very fast. Apparently, most of the NaF aggregates are near the surface of the fibers and the dissolved NaF is exuded easily from the fiber.

Use in Brushes

Brushes were made with the fibers made in accordance with the methods described in regard to Fibers #1–4. Fibers of appropriate length were bundled and placed in a handle by conventional means.

These brushes were evaluated for release of NaF in a setting to simulate oral brushing.

A highly polished stainless steel block was cleaned in an ultrasonic cleaning solution for 10 minutes with a dental general purpose cleaner, and sonicated in a glass beaker with triple-distilled deionized water (3DD $H_2O$) for six rinses prior to each trial.

The block was immersed in 100 ml simulated saliva (SSS) for five minutes prior to each test. The SSS was tested after this five minute period for sodium fluoride concentration.

While the block was in the 100 ml of SSS, the brush was scrubbed against the corrugated block twice for 20 seconds on each side of the block in order to assess the amount of release of the high concentration NaF from the PVA bristle. The procedure is repeated sixteen times a day. Sixteen brushings is the equivalent of brushing all four tooth quadrants on the inside and outside of the teeth twice a day. The interval between brushings was five seconds.

Following each brushing the block was removed and placed in 100 ml of 3DD $H_2O$ and sonicated for five minutes to remove all traces of sodium fluoride from the surface. The 3DD H₂O was used for this rinsing of the corrugated blocks was assessed previously for NaF concentration before any use. The 3DD H₂O was added to the 100 ml of SSS. SSS/3DD H₂O solution was assessed for NaF in ppm.

Figure 9:
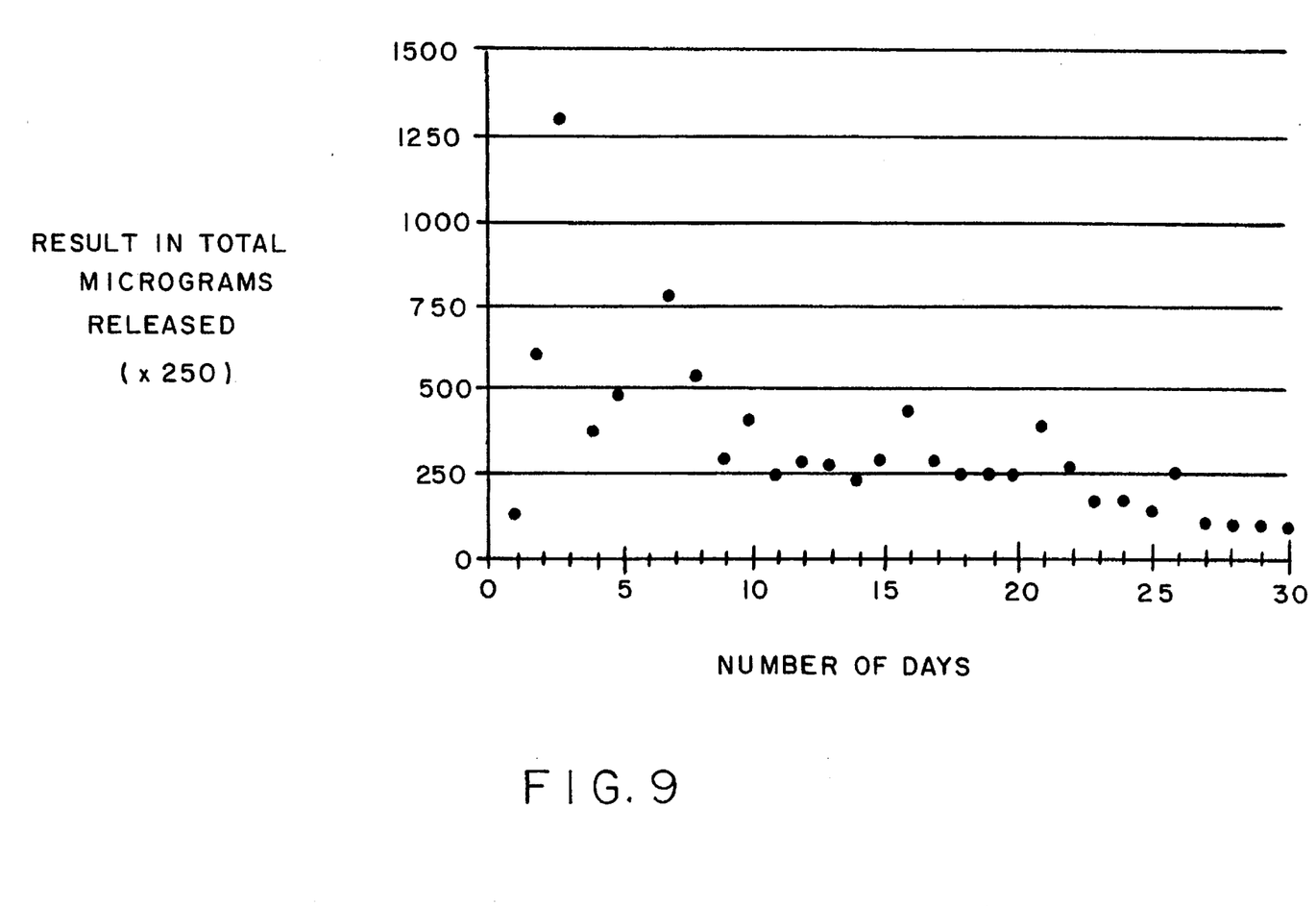
FIGS. 9–12 depict graphically the release of NaF from brushes made in accordance with the present invention.

FIG. 9 graphically depicts the release of NaF from brushes made from fiber #1. Fiber #1 was made with an inner core having a high concentration of NaF, and an outer shell with little or no NaF.

Figure 10:
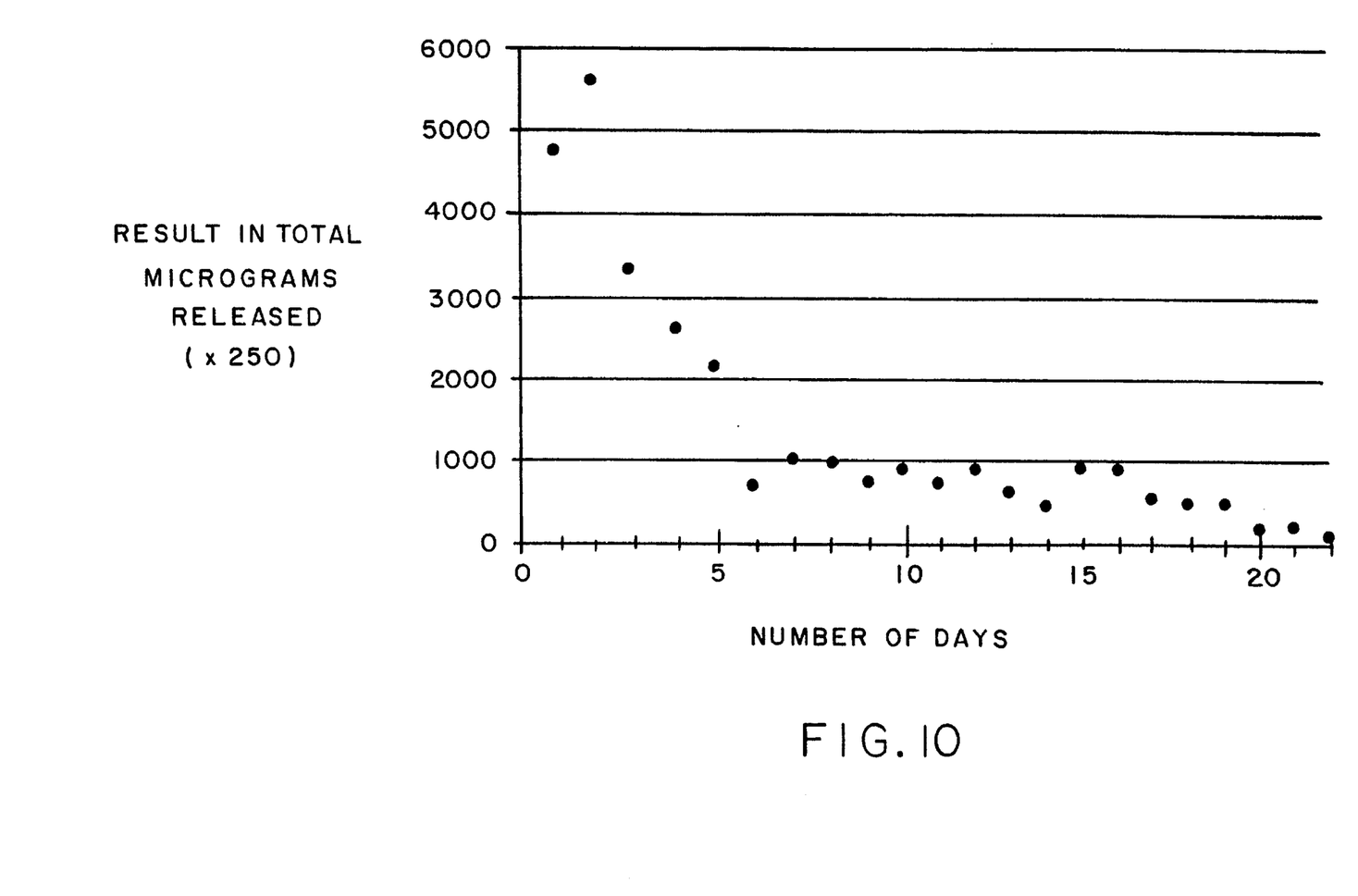

FIG. 10 graphically depicts the release of NaF from brushes made from fiber #2. Fiber #2 was made with a homogeneous distribution of NaF in a PVA matrix.

Figure 11:
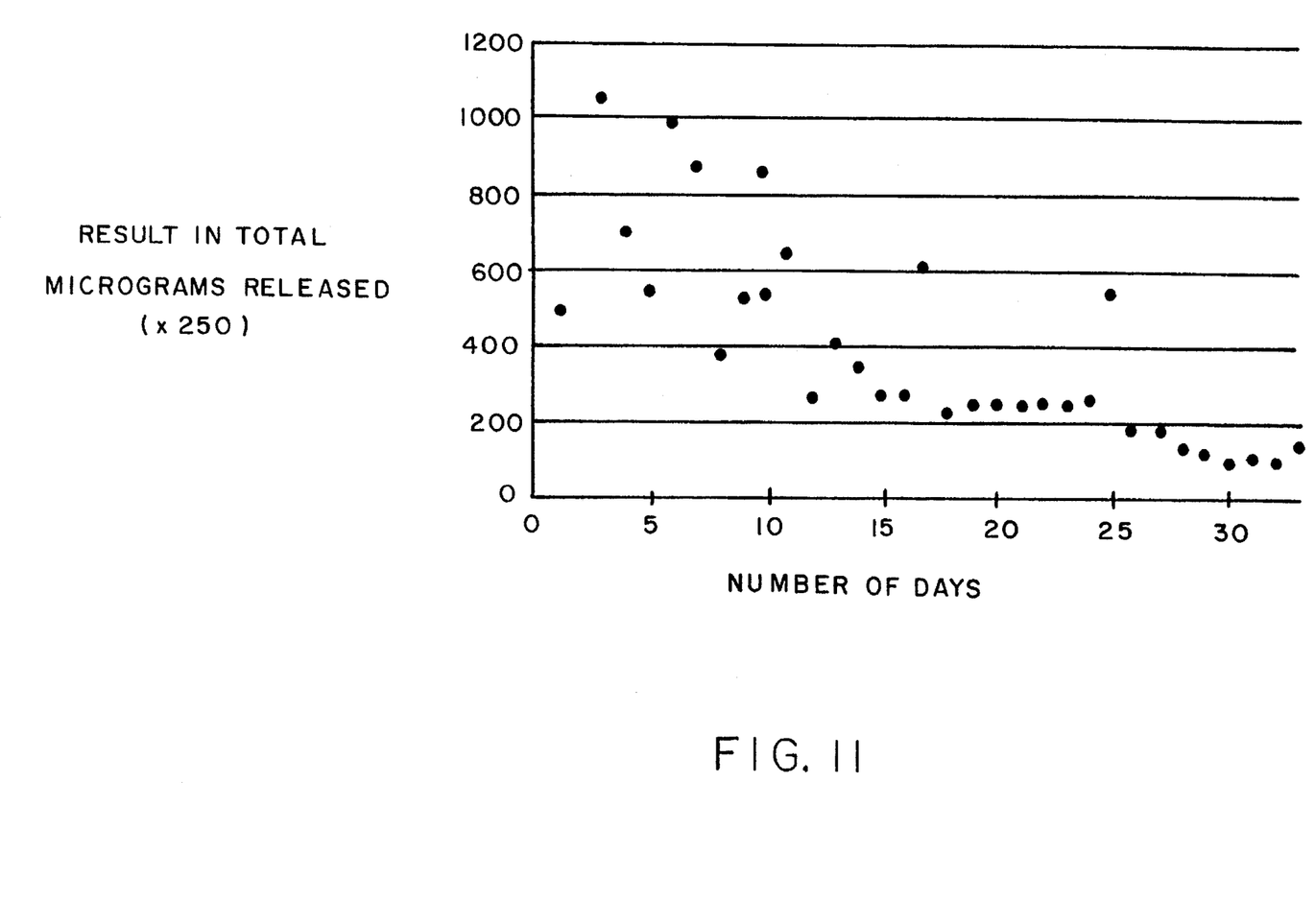

FIG. 11 graphically depicts the release of NaF from the brushes made from fiber #3. Fiber #3 was made with a core having a high concentration of NaF, including crystals, and an outer shell with little or NaF.

Figure 12:
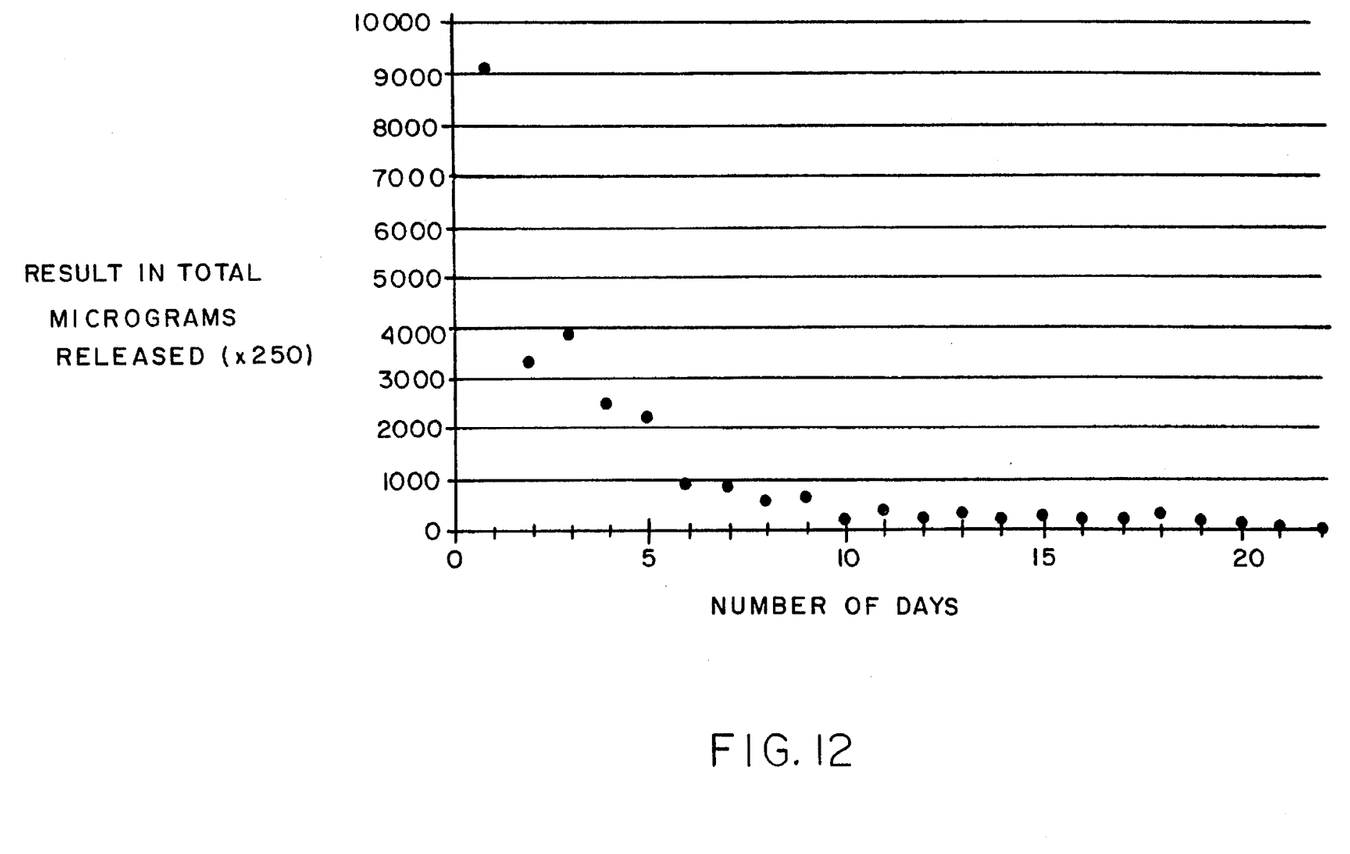

FIG. 12 graphically depicts the release of NaF from fiber #4. Fiber #4 was made by incorporating NaF into the PVA matrix by swelling.

As illustrated in FIGS. 9–12, each brush is made with fiber #1, fiber #2, fiber #3, and fiber #4 exhibited an initial burst of release of NaF. Leading to the burst, initial brushings may release little to approximately 125 mg NaF per brushing. After one or two brushings, subsequent brushings may release as much as 1250 mg per brushing. The initial burst tapers off through days 5–10. The release of NaF during the tapering off period may range from 750–250 mg per brushing. The typical release pattern exhibits a plateau from day 10 through day 30. During the plateau period, the release ranges from 250–100 mg per brushing.

Thus while preferred embodiments of the invention have been described, the present invention is capable of variation and modification and therefore, the present invention should not be limited to the precise details set forth, but should include such changes and alterations as fall within the purview of the following claims.

What is claimed is:

1. A floss for delivery of a drug to the oral cavity for application to teeth and other dental applications comprising:

a string having a plurality of fibers, at least one of said fibers comprising a polyvinyl alcohol matrix holding a drug, said polyvinyl alcohol matrix formulated for application to the oral cavity to release said drug in the presence of oral secretions, said drug selected from the group consisting of sodium fluoride, stannous fluoride, quarternary ammonium compounds, essential oils, sanguinarine and bisbiguanides.

2. The floss of claim 1 wherein said bisbiguanides are selected from the group consisting of chlorhexadine and alexidrine.

3. A method of administering a drug to the oral cavity comprising administering a drug held in a polyvinyl alcohol matrix to the oral cavity of a subject in need thereof, said polyvinyl alcohol matrix in the form of one or more fibers of a string for use as a floss, said drug selected from the group consisting of sodium fluoride, stannous fluoride, quarternary ammonium compounds, essential oils, sanguinarine and bisbiguanides, said drug released from said matrix as said string is applied in the oral cavity as a floss.

4. The method of claim 3 wherein said bisbiguanide is selected from the group consisting of chlorhexadine, alexidrine.

5. A method of making a floss for the delivery of a drug comprising:

forming a matrix of polyvinyl alcohol having a drug or loading a drug into a polyvinyl alcohol matrix, drawing said matrix into a fiber and in incorporating said fiber into a string for use as a floss for the oral cavity.

6. The floss of claim 1 wherein said matrix has an interior area and an exterior area, said drug having a higher concentration in the interior area of said matrix than said exterior area.

7. The floss of claim 1 wherein said drug is distributed throughout the polyvinyl alcohol matrix.

8. The method of claim 3 wherein said drug is distributed as aggregates in the matrix.

9. The method of claim 3 wherein said matrix has an interior area and an exterior area, said drug having a higher concentration in said interior area than said exterior area.

10. The method of claim 3 wherein said drug is selected from the group consisting of sodium fluoride and stannous fluoride.

* * * * *